United States Patent [19]

Barsa et al.

[11] 4,046,858

[45] Sept. 6, 1977

[54] SYNTHESIS FOR CRYSTALLINE HYDROXYAPATITE

[76] Inventors: John J. Barsa, 133 Blaisdell Road, Orangeburg, N.Y. 10962; Edward T. Farris, 2541 Sweetbriar Road, Dallas, Tex. 75228; Richard J. Lagow, 21 Magnolia Ave., Manchester, Mass. 00144

[21] Appl. No.: 491,581

[22] Filed: July 24, 1974

[51] Int. Cl.² .................... C01B 15/16; C01B 25/26
[52] U.S. Cl. ................................. 423/305; 423/307; 423/311
[58] Field of Search ................... 423/305, 307–313

[56] References Cited

U.S. PATENT DOCUMENTS

| 2,277,778 | 3/1942 | Randall | 423/307 |
| 3,539,291 | 11/1970 | Chiola | 423/307 |
| 3,737,516 | 6/1973 | Jenner | 423/308 |

FOREIGN PATENT DOCUMENTS

| 40-8613 | 8/1965 | Japan | 423/311 |

Primary Examiner—Earl C. Thomas
Assistant Examiner—Gregory A. Heller
Attorney, Agent, or Firm—David E. Brook

[57] ABSTRACT

A new synthesis is disclosed which produces synthetic crystalline hydroxyapatite. The process comprises reacting anhydrous trisodium phosphate wih calcium chloride in a formamide/water solution. Good yields of hydroxyapatite are obtained quickly, simply, and at low temperatures.

4 Claims, No Drawings

SYNTHESIS FOR CRYSTALLINE HYDROXYAPATITE

BACKGROUND OF THE INVENTION

1. Field of the Invention

This invention relates to the production of a tooth restorative material and more particularly to the production of synthetic hydroxyapatite.

2. Description of the Prior Art

Traditionally, tooth cavities have been filled with silver or gold amalgam materials. Such amalgams are, however, far from ideal tooth restorative materials. From a cosmetic point of view, for example, these materials do not match the existing teeth in color. From a functional point of view, they are also inferior since their physical properties, such as heat conductivity, coefficient of expansion, etc., are markedly different from the physical properties of tooth enamel.

Recently, researchers have attempted to develop new tooth restorative materials having better properties than the existing silver or gold amalgams. Three such materials include the silica cements, methyl methacrylate based resins, and combinations of fused silica powder bound together in cross-linked organic polymers. The latter are thoroughly described in patents issued to Rafael L. Bowen. See U.S. Pat. Nos. 3,066,112; 3,194,783; and, 3,194,784.

Despite these attempts to product better tooth restorative materials, the compositions produced to date have not proven to be entirely satisfactory. This is probably because of the many stringent requirements which must be met by successful tooth restorative materials.

The best possible dental restorative would be synthetically produced tooth enamel. Natural tooth enamel is considered to be tightly packed crystals of hydroxyapatite. People have, of course, recognized this and attempted to grow crystalline hydroxyapatite synthetically. While such growth has been accomplished, the yields have been exceptionally small and the syntheses have required long lengths of time, high pressurs and/or high temperatures.

Several prior art attempts to prepare crystalline hydroxyapatite synthetically are described in the literature. Thus, it has been shown that the formation of crystalline hydroxyapatite can be divided into two distinct stages in aqueous solution from the dissolution of non-crystalline calcium phosphate. In the first stage, the crystals grow by a diffusion controlled dendritic mechanism resulting in the production of a colloidal apatite particle. These apatite crystals continue to grow through a consolidation process known as Ostwald ripening. This process is exceptionally slow, as noted by the statements by the authors that the crystals increased in size from 120 A at the onset of the post-conversion period to only 251 A by the end of 70 days. See Eanes, E. D. and Posner, A. S.; "A Note on the Crystal Growth of Hydroxyapatite Precipitated from Aqueous Solutions;" *Materials Research Bulletin;* Vol. 5; pp. 377-384; 1970; Pergamon Press.

In another prior art process, synthetic, crystalline hydroxyapatite is formed from calcium phosphates under conditions of high pH and high initial concentrations of reactants. Three stages are involved and the third stage, which involves the conversion of an amorphous precursor to crystalline hydroxyapatite, doesn't begin until after seven hours of reaction, and is said to continue indefinitely by the authors. See Eanes, E. D. Gillessen, I. H. and Posner, A. S.; "Intermediate States in the Precipitation of Hydroxyapatite;" *Nature;* Vol. 5008; Oct. 23, 1965; pp. 365-367.

The slow nature of these syntheses is further described by Nancollas, G. H. and Mohan, M. S. in "The Growth of Hydroxyapatite Crystals;" *Archives of Oral Biology;* Vol. 15; pp. 731-745; 1970; Pergamon Press.

Some attempts to use hydrothermal bombs have been described. These employ extremely large pressures and high temperatures, but still have resulted in low yields and long times. See, for example: Kirn, J. F. and Keidheiser, Jr., H.; "Progress in Efforts to Grow Large Single Crystals of Hydroxyapatite;" *Journal of Crystal Growth;* Vol. 2; pp. 111-112; 1968; North-Holland Publishing Co.; and, Perloff, A. and Posner, A. S.; "Preparation of Pure Hydroxyapatite Crystals;" pp. 583-584.

As can be appreciated from the above discussion, there is a great need for a simple, controllable, reliable and speedy synthesis for crystalline hydroxyapatite. In fact, the Perloff and Posner article cited above states: "A simple method for the production of pure well-crystallized hydroxyapatites has long been needed."

SUMMARY OF THE INVENTION

The invention comprises a new process for directly synthesizing crystalline hydroxyapatite. This synthesis is accomplished by reacting anhydrous trisodium phosphate, $Na_3PO_4$, with calcium chloride in a formamide/water solution.

A significant advantage of the synthesis is that it starts spontaneously and continues in a steady manner; the precipitation of hydroxyapatite continues as long as reactants are supplied. Other desirable features of the process are that it can be carried out at low temperatures and that it is a simple process. Additionally, the process provides a method of bonding a synthetically produced tooth restorative directly to natural tooth enamel.

The most important advantage of this process is that it produces synthetic crystalline hydroxyapatite in significant amounts which are identical to natural tooth enamel. Thus, the process provides a supply of the one ideal tooth restorative material.

DESCRIPTION OF THE PREFERRED EMBODIMENTS

Crystalline hydoxyapatite can be represented by the empirical formula, $Ca_{10}(PO_4)_6(OH)_2$. From this formula, it is clear that any synthesis for hydroxyapatite must include reactants which function as sources of calcium and phosphate.

The source of phosphate used in this synthesis is anhydrous trisodium phosphate, $Na_3PO_4$. Anhydrous trisodium phosphate is chosen because of its outstanding solubility in the solvents used, which are described in more detail infra. Calcium salts, such as calcium chloride, calcium thiocyanate and calcium nitrite are suitable sources of calcium. Calcium chloride is a preferred material since it has been found to result in outstanding crystalline hydroxyapatite.

Stoichiometric amounts of trisodium phosphate and calcium salts are preferred because of the excellent product they produce. Thus, about 1.64 grams of the phosphate are typically used with about 30 milliliters of one molar solution of calcium chloride. Varying the relative amounts of reactants in either direction tends to yield inferior hydroxyapatite. Thus, higher concentrations of calcium ions results in crystal attack yielding a disorderly product. Smaller concentrations of calcium do not react to produce the crystalline hydroxyapatite desired.

A combination solvent has been found to be essential to produce crystalline hydroxyapatite which contains from 25 to 90% water, and from 10;14 75% of a polar, aprotic, organic solvent. Some examples of suitable organic solvents include formamide, dimethyl sulfoxide, and dimethyl formamide. The most preferred organic solvent has been found to be formamide, and a preferred combination is a 50/50 mixture of water and formamide.

If the organic solvent is used alone, the product is not crystalline hydroxyapatite but is a chlorine containing apatite. The best crystallizations result with pure organic solvent, and as water is added the crystallizations become poorer but do produce larger amounts of crystalline hydroxyapatite.

The temperatures involved in the synthesis can be varied widely. If the reactants are mixed at room temperature, precipitation of crystalline hydroxyapatite typically begins immediately. It is possible, of course, as with any chemical reaction, to use elevated temperatures if desired.

It is not fully understood why the particular types of reactants and solvent as described herein combine to produce crystalline hydroxyapatite whereas the prior art has had so much problem producing this material. As mentioned above, prior art methods often resulted in the precipitation of an unstable, colloid-like, intermediate material. One possible explanation has not been proved but which is offered as an aid to understanding the process, is as follows. In prior art processes it was customary to mix aqueous solutions of calcium and sodium ions. Upon mixing these solutions, the solvent (water) molecules might have positioned themselves around the ions to form a solvation complex which altered the ion-association sequence so that the unstable colloidal intermediate precipitated. On the other hand, by attacking crystals of amorphous trisodium phosphate with a formamide solution, this solvation complex is altered to change the ion-association sequence and resulting in the direct precipitation of crystalline hydroxyapatite.

Synthetic crystalline hydroxyapatite produced as described herein is useful as a tooth restorative and also is useful as a material from which caps, dentures, etc. can be formed.

Those skilled in the art of dental restoration will know or be able to ascertain by no more than routine experimentation, suitable techniques for applying synthetically produced crystalline hydroxyapatite to teeth. Such material may be, for example, precipitated directly at predetermined locations on teeth, or may be mixed with suitable binders and applied with an adhesive to existing teeth. A significant advantage of these materials is the outstanding bonding to natural teeth enamel which can be expected.

The following example further illustrates the invention.

EXAMPLE 1

A 1.0 molar calcium chloride solution is prepared wherein the solvent comprises 50% formamide and 50% water. At room temperature, about 1.64 grams of anhydrous trisodium phosphate was added to 30 milliliters of the calcium chloride solution. Fine white crystals of hydroxyapatite, $Ca_{10}(PO_4)_6OH$, immediately began to form. Precipitation continued until the supply of sodium phosphate was exhausted.

The crystals were recovered by extraction with ethanol, followed by washing with water.

An X-ray powder pattern diffraction analysis was conducted using a Phillips' Electronic Instrument, type 52019/0 analyzer. Samples of the crystals were ground up, placed in a glass capillary, mounted in a powder diffraction camera with a nickel window and a copper source. The resulting X-ray powder pattern was identical to that produced by ground human teeth. It was also identical to a commercial product sold by Mallinkropdt under the name "Calcium Phosphate, Tribasic, $Ca_{10}(OH)_2PO_4$, Analytical Reagent," (which is crystalline hydroxyapatite), and was also identical to that shown for hydroxyapatite at set 9, compund 432, page 542 of *Powder Diffraction File, Sets 6–10 (Revised);* published by Joint Committee on Powder Diffraction Standards of ASTM, Am. Cryst. Assoc.; The Inst. of Physics, and Nat'l. Assoc. of Corr. Engrs.; (1967).

What is claimed is:

1. A process for preparing crystalline hydroxyapatite comprising contacting a source of calcium ions with about a stoichiometric amount of anhydrous trisodium phosphate in a combination solvent comprising from about 10 to about 75 weight percent of a polar, aprotic organic solvent and from about 25 to about 90 weight percent of water and thereafter recovering said crystalline hydroxyapatite.

2. The process of claim 1 wherein said polar, aprotic, organic solvent consists essentially of formamide.

3. The process of claim 2 wherein said source of calcium ions consists essentially of calcium chloride.

4. The process of claim 3 wherein said combination solvent consists essentially of about 50 weight percent formamide and about 50 weight percent water.

* * * * *